(12) United States Patent
Kula et al.

(10) Patent No.: US 9,314,757 B2
(45) Date of Patent: Apr. 19, 2016

(54) METHOD AND A DEVICE FOR GENERATING A CARBURIZING GAS MIXTURE

(75) Inventors: Piotr Kula, Łódź (PL); Robert Pietrasik, Brzeziny (PL); Łukasz Kaczmarek, Łódź (PL); Agnieszka Głądka, Łowicz (PL); Maciej Korecki, Świebodzin (PL)

(73) Assignees: SECO/WARWICK S.A., Świebodzin (PL); POLITECHNIKA LODZKA, Lodz (PL)

( * ) Notice: Subject to any disclaimer, the term of this patent is extended or adjusted under 35 U.S.C. 154(b) by 0 days.

(21) Appl. No.: 13/455,743

(22) Filed: Apr. 25, 2012

(65) Prior Publication Data

US 2012/0283495 A1    Nov. 8, 2012

(30) Foreign Application Priority Data

May 5, 2011    (PL) .......................................... 394787

(51) Int. Cl.
*C07C 5/00* (2006.01)
*C07C 5/02* (2006.01)
(Continued)

(52) U.S. Cl.
CPC .. *B01J 3/03* (2013.01); *B01J 8/025* (2013.01); *B01J 8/0285* (2013.01); *C07C 5/09* (2013.01);
(Continued)

(58) Field of Classification Search
CPC .............. C07C 5/00; C07C 5/02; C07C 5/03; C07C 5/05; C07C 5/09; C07C 11/04; C07C 11/24; C07C 2523/42; C07C 2523/44; B01J 3/03; B01J 8/025; B01J 8/0285; B01J 2208/00371; B01J 2208/00061; B01J 2208/00548

USPC .................................. 585/262, 250, 258, 259
See application file for complete search history.

(56) References Cited

U.S. PATENT DOCUMENTS

| 6,350,717 | B1 * | 2/2002 | Frenzel et al. ................. 502/330 |
| 2003/0055302 | A1 | 3/2003 | Cheung et al. |
| 2009/0326288 | A1 * | 12/2009 | Mamadov et al. ............. 585/259 |

FOREIGN PATENT DOCUMENTS

| EP | 1 787 949 A2 | 5/2007 |
| WO | WO 2004/035853 A1 | 4/2004 |

OTHER PUBLICATIONS

Hysafe, Biennal Report on Hydrogen Safety, Hydrogen Safety Barriers and Safety Measures, Chapter V, May 2006.*

Seider, W; Seader, J.D; Lewin, D., Widagdo, S., "Product and Process Design Principles," Third Edition, 2009, p. 164-165.*

(Continued)

*Primary Examiner* — In Suk Bullock
*Assistant Examiner* — Philip Louie
(74) *Attorney, Agent, or Firm* — Oliff PLC

(57) ABSTRACT

A method to generate a ternary carburizing gas mixture, using a reaction of selective hydrogenation of acetylene in a stream of hydrocarbons to the form of ethylene, comprising the following steps: heating of the inside of the reactor with an inert gas to an operating temperature for a period of 20 minutes at a temperature of 300° K, passing a mixture of hydrogen and acetylene by the regiospecific catalyst, and moving out the reaction products on the outside after passing the mixture through the regiospecific catalyst, but generation is effected in a continuous mode in the operating temperature range of the regiospecific catalyst between 293° K and 398° K, preferably at a temperature of 350° K.

10 Claims, 1 Drawing Sheet

(51) Int. Cl.
*C07C 5/09* (2006.01)
*B01J 3/03* (2006.01)
*B01J 8/02* (2006.01)

(52) U.S. Cl.
CPC .................. *B01J 2208/00061* (2013.01); *B01J 2208/00371* (2013.01); *B01J 2208/00548* (2013.01); *C07C 2523/42* (2013.01); *C07C 2523/44* (2013.01)

(56) References Cited

OTHER PUBLICATIONS

Seider, W; Seader, J.D; Lewin, D., Widagdo, S., "Product and Process Design Principles," Third Edition, 2009, p. 164-167.*
Feb. 12, 2013 European Search Report issued in European Application No. 12 002 928.5.

* cited by examiner

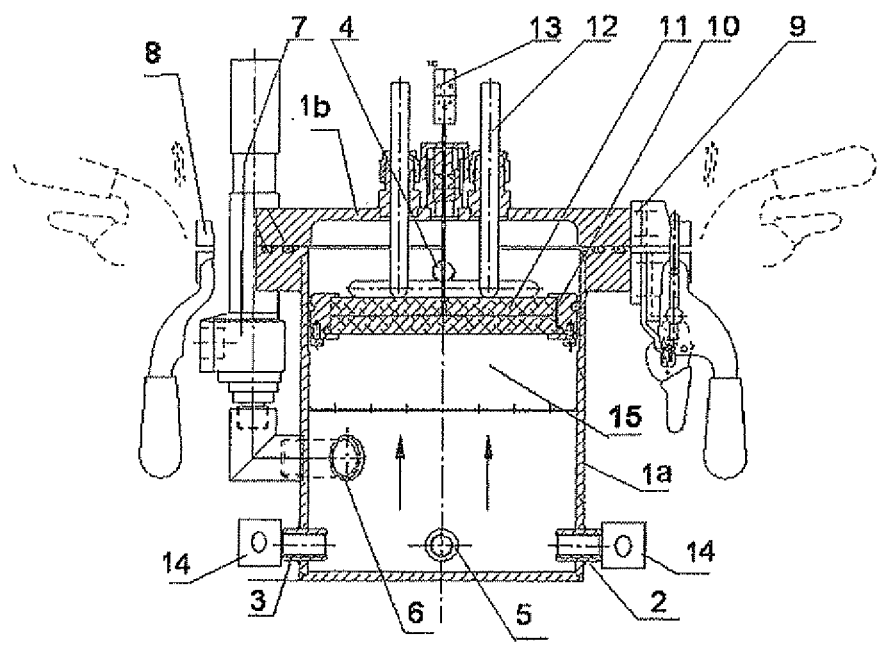

METHOD AND A DEVICE FOR GENERATING A CARBURIZING GAS MIXTURE

The present invention relates generally to metallurgical processes and more particularly to a synthesis of the ternary carburizing gas mixture and a device for generating a ternary carburizing gas mixture.

A carburizing mixture, which is indispensable in the carburizing technology, provides just one possibility of thermal treatment intended to improve the mechanical properties of the superficial layers of metals, particularly metal details working in frictional units exposed to contact stress conditions.

Carbon-rich gases such as methane, acetylene, ethylene, or propane, are used as the operating atmosphere in the obtaining of atomic carbon in conventional processes.

An acetylene decomposition reaction, proceeding in a single step, produces hydrogen which is an only product being generated apart from carbon and which it is not a great problem to remove. Ethylene is the third gas used in vacuum carburizing processes. Ethylene decomposition is much more simple, compared with that of propane and does not lead to the formation of soot or tar.

A number of analyses and studies addressing the problem of how to avoid the formation of soot or tar and eliminate internal oxidation have led to the application of carburizing atmosphere, which is discussed in the Polish Patent No. 204202, also published as the U.S. Pat. No. 7,513,958. According to the said patents, a process is described to generate a ternary carburizing mixture of two unsaturated hydrocarbons and hydrogen, the ratio of the unsaturated hydrocarbons being in the range acetylene:ethylene from 0.1 to 2.0, the most preferable composition being 40% C2H2:40% C2H4: 20% H2. The said mixture is obtained by feeding the gases in suitable ratios.

Another method consists in the possibility of a prior preparation of ethylene as one of the substrates by the method referred to in the U.S. Pat. No. 7,513,958 by methane pyrolysis, ethanol dehydroxylation, elimination of dialkyl halides with halogen compounds, as well as by way of petroleum refining. However, such methods are rather complicated.

Another method to obtain ethylene, too, as one of the substrates is the selective hydrogenation of acetylene to the form of ethylene by the "front-end" or "tail-end" method, as disclosed in the U.S. Pat. No. 6,509,292. The reaction proceeds at a high excess of hydrogen in the former case while a slight surplus of hydrogen is used in the second case. The method is applied only for the removal of any contaminants from ethylene, specifically in the form of acetylene; the presence of any residual amount of acetylene has a negative impact on the C2H4 polymerization process.

Disclosed in the Polish Patent 198889 are devices for selective hydrogenation, based on a catalyst which comprises gallium oxide and in which platinum is the active component preferably used in the amount of 5% by weight.

Disclosed in the U.S. Pat. No. 5,510,550, No. 5,856,262, and No. 7,453,017 are selective hydrogenation devices based on catalysts in which a transition metal in the form of Pd, Pt, in the amount of 0.05 to 2.0% by weight is supported on a ceramic support with a highly developed surface.

Disclosed in the U.S. Pat. No. 7,038,097 are also designs of devices in which the acetylene hydrogenation process (to 2.0% in the mixture) is carried out in two-steps using two different catalysts: one for the preliminary hydrogenation of, mainly oligomers, and the other for the hydrogenation and preparation of reaction products in the form of 100% saturated compounds.

Disclosed in the Polish Patent No. 192732 are also devices for the selective hydrogenation of highly unsaturated compounds in a stream of hydrocarbons, based on a column distillation reactor, comprising a layer of a hydrogenation catalyst, the said hydrogenation catalyst being a catalyst comprising from 0.1 to 5.0% by weight of palladium oxide, supported on aluminium oxide drawpieces, and the said process is carried out, preferably, at relatively low temperatures and elevated pressure conditions. The gist of the method of the invention is that, initially, any atmosphere remaining inside the reactor is removed by means of an outlet pipe and then, the inside of the reactor is heated using an inert gas up to a working temperature for a period of 20 minutes at 300° K, whereupon a hydrogen-acetylene mixture is made to flow through a regiospecific catalyst and reaction products are taken outside after passing the mixture through the regiospecific catalyst, while the generation process is carried out in a continuous mode at the working temperature of the regiospecific catalyst in the range from 293° K to 398° K, preferably at 350° K.

Preferably, the inert gas to be introduced into the reactor is either nitrogen or argon or helium.

Also preferably, heating by means of the inert gas is resumed in the course of the process.

Furthermore, preferably, the course of the process is controlled and synchronized remotely, preferably by means of a computer network and/or the Internet.

Also preferably, the mixture is obtained by mixing the following pure gases: acetylene and hydrogen.

Furthermore, the mixture is preferably obtained in a flow rate range from 60 ml/min to 25 l/min.

Also preferably, a mixture is prepared which comprises 45-55% of acetylene and 55-45% of hydrogen, respectively.

Furthermore, the pressure inside the reactor is preferably held in the range from 0.25 MPa to 10 MPa.

Moreover, the pressure inside the reactor is preferably held below 0.25 MPa.

The essence of the device generating the ternary carburizing mixture of the invention is that a cooling system is located under the cover of the reactor housing above the regiospecific catalyst in such a manner that the porous regiospecific catalyst support is located exactly between the lower part of the reactor housing and the cover, moreover, the working temperature range in the region of contact between the regiospecific catalyst and the support is from 293° K to 398° K, preferably 350° K, and is controlled by means of a thermocouple, the cover of the reactor in the working status is tightly closed, and the reactor is filled with acetylene and hydrogen being provided by means of inlet pipes.

Preferably, the regiospecific catalyst is a uniform, continuous catalyst bed having a surface thickness.

Also preferably, the regiospecific catalyst is made of palladium or platinum.

Furthermore, the inlet pipe set and/or the outlet pipes are multiple.

Also preferably, the regiospecific catalyst is used in a saturation range from 1 to 10%, preferably 5%.

Also preferably, the tight closure of the cover is provided by clamps.

Also preferably, the clamps are adjusted mechanically or by means of pressure.

Also preferably, the mass flow valves and the safety valve are synchronized.

In addition, the working temperature is preferably controlled by synchronization of the thermocouple and the cooling system.

Furthermore, adjustment and synchronization are preferably carried out remotely and preferably by means of a computer network and/or the Internet.

It was found that it is possible to generate the carburizing mixture directly in the low-pressure carburizing process, the generating of such mixture guarantees the process good rate and repeatability, and that the best efficiencies of the process of selective hydrogenation of acetylene to ethylene are obtained for a feed mixture in the concentration ratio of 46% of acetylene $C_2H_2$ and 54% of hydrogen.

In addition, the device is much less complicated and hence safer in operation, compared with devices designed for "methane pyrolysis, ethanol dehydroxylation, elimination of dialkyl halides with halogen compounds, as well as petroleum refining" and, moreover, it provides an ethylene product with yields above 70% either in a continuous or batch manner.

The device of the invention will now be discussed in more detail in the embodiment illustrated in the FIGURE showing a diagram of the device, and the method of the invention will be illustrated in the three procedures below.

The device designed for generating a ternary carburizing mixture is a reactor 15 with housing 1a, 1b. A regiospecific catalyst 11 is supported on support 10 inside the reactor 15 housing. The reactor 15 is equipped with a set of inlet pipes 2, 3 with mass flow valves 14 for the supply of gases and it has an outlet pipe 4 above the catalyst enabling the collecting of reaction products, so that the outlet pipe 4 is located on the opposite sides of the catalyst with respect to the inlet pipes 2, 3, and it is provided with an outlet pipe 6 to the atmosphere, connected with the safety valve 7. A cooling system 12 is located under the cover 1b above the regiospecific catalyst 11, the support of the regiospecific catalyst 11 has a porous structure and is located exactly between the lower part 1a and the cover 1b. Operating temperature in the region of contact between the regiospecific catalyst 11 and the support 10 is set at 350° K and is controlled using a thermocouple 13, so that the cover 1b is tightly closed when the reactor 15 is in the working status and the reactor is supplied with acetylene and hydrogen via inlet pipes 2 and 3. The regiospecific catalyst 11 is a uniform and continuous bed of a surface thickness and is made of palladium with a 5% saturation. A complete set of inlet pipes 2, 3, 5 and/or the outlet pipes 4, 6 are single, and the tight closure of the cover 1b is obtained mechanically by means of clamps 9, so that mass flow valves 14 and the safety valve 7 are synchronized and, moreover, the operating temperature is controlled by means of synchronization of the thermocouple 13 and the cooling system 12.

After any atmosphere remaining inside the reactor is removed and taken out via the outlet pipe to the atmosphere 6, in a continuous manner, at the catalyst's operating temperature of, optimally, 350° K, the inside of the reactor 15 is heated to the operating temperature for a period of 20 minutes using an inert gas being supplied by one inlet pipe 5, then hydrogen is supplied to the inside of the reactor by one more inlet pipe 2 and acetylene is supplied by another inlet pipe 3. A mixture of hydrogen and acetylene is then made to flow through the regiospecific catalyst 11 and reaction products are taken out by means of the outlet pipe 4 after passing through the regiospecific catalyst 11. Nitrogen is the inert gas. The pressure inside the reactor 15 is lower than 0.25 MPa.

EXAMPLE I $N_2$ at a temperature of 300° K was passed for 20 minutes through the reactor 15, packed with the regiospecific catalyst Pd 11, supported on the porous support 10. After closing the valve on the pipe 5, the valve on the pipes 2 and 3 was opened and then acetylene at a flow rate of 40 ml/min and hydrogen at a flow rate of 20 ml/min were passed onto the regiospecific catalyst 11 in the amount of 0.05 mg to obtain a ternary mixture of unsaturated hydrocarbons at the ratio of acetylene:ethylene of 0.6 with hydrogen at a temperature of 350° K. The regiospecific catalyst used was 5% palladium, supported on the 10 $Al_2O_3$ porous support.

EXAMPLE II

Following the procedure of Example I, the valve on the pipes 2 and 3 was opened to supply acetylene at the flow rate of 1000 ml/min and hydrogen at the flow rate of 1500 ml/min onto the regiospecific catalyst 11 in the amount of 0.8 mg to obtain a ternary mixture of unsaturated hydrocarbons at the ratio of acetylene to ethylene of 1.96 with hydrogen at a temperature of 350° K. The regiospecific catalyst used was 5% palladium, supported on the 10 $Al_2O_3$ porous support.

EXAMPLE III

Following the procedure of Example I, the valve on the pipes 2 and 3 was opened, to supply acetylene at the flow rate of 10000 ml/min and hydrogen at the flow rate of 11410 ml/min onto the regiospecific catalyst 11 in the amount of 4.5 mg to obtain a ternary mixture of unsaturated hydrocarbons at the ratio of acetylene to ethylene of 1.48 with hydrogen at a temperature of 398° K. The regiospecific catalyst used was 5% palladium, supported on the 10 $Al_2O_3$ porous support.

LIST OF INDICATIONS

1a—lower part of housing
1b—cover of housing
2—inlet pipe for acetylene
3—inlet pipe for hydrogen
4—outlet pipe for reaction products
5—inlet pipe for inert gas
6—outlet pipe to atmosphere
7—safety valve
8—clamp
9—clamp
10—regiospecific catalyst support
11—regiospecific catalyst
12—cooling system
13—thermocouple
14—safety valve
15—reactor

The invention claimed is:
1. A method for generating a ternary carburizing gas mixture, the method comprising:
  removing atmosphere from inside a reactor, the inside of the reactor containing a layer of a regiospecific hydrogenation catalyst comprising palladium or platinum,
  heating the inside of the reactor to an operating temperature of the catalyst with heated inert gas,
  hydrogenating at least a portion of a reactant mixture consisting of 45 to 55% hydrogen and 55 to 45% acetylene, respectively, in the presence of the regiospecific catalyst to selectively catalyze the hydrogenation of a portion of the acetylene into ethylene and produce the carburizing gas mixture, and
  removing the ternary carburizing gas mixture from the reactor;

wherein:
generating the ternary carburizing gas mixture is carried out in a continuous mode at an operating temperature range of the regiospecific catalyst between 293 K and 398 K; and the generated ternary carburizing gas mixture has a ratio of acetylene to ethylene in a range of 0.6 to 2.0.

2. The method according to claim 1, wherein the inert gas is nitrogen, argon or helium.

3. The method according to claim 1, wherein heating with the inert gas is resumed during the continuous mode.

4. The method according to claim 1, wherein the reactant mixture is obtained by mixing pure acetylene gas and pure hydrogen gas.

5. The method according to claim 1, wherein a flow rate of the reactant mixture is in a range of between 60 ml/min and 25 l/min.

6. The method according to claim 1, wherein a pressure inside the reactor is maintained in a range between 0.25 MPa and 10 MPa.

7. The method according to claim 1, wherein a pressure inside the reactor is maintained below 0.25 MPa.

8. The method according to claim 1, wherein a device designed for generating a ternary carburizing gas mixture is used, the device comprising:

a reactor with a housing and packed with a regiospecific catalyst on a support inside the reactor housing, equipped with a complete set of inlet pipes with mass flow valves to supply gases and a first outlet pipe above the catalyst for taking out the reaction products, so that the first outlet pipe is located on an opposite sides of the catalyst with respect to the inlet pipes, and a second outlet pipe to an atmosphere connected with a safety valve, wherein there is a cooling system under a cover of the reactor housing, above the regiospecific catalyst so that a porous support of the regiospecific catalyst is located exactly between a lower part of the housing of the reactor and its cover, furthermore, the working temperature range in the region of contact between the regiospecific catalyst and the support is from 293 K to 398 K and is controlled by a thermocouple, the cover of the reactor in a working status is tightly closed, and the reactor is filled with acetylene and hydrogen provided by inlet pipes for acetylene and hydrogen.

9. The method according to claim 8, wherein the regiospecific catalyst is a uniform and continuous bed having a surface layer.

10. The method according to claim 8, wherein the regiospecific catalyst is used in a saturation range from 1 to 10%.

* * * * *